United States Patent [19]

Weisenfeld

[11] Patent Number: 5,723,049
[45] Date of Patent: Mar. 3, 1998

[54] TREATMENT OF A FORMALDEHYDE-CONTAINING WASTE STREAM

[75] Inventor: Robert B. Weisenfeld, Chesterfield, Mo.

[73] Assignee: Monsanto Company, St. Louis, Mo.

[21] Appl. No.: 718,608

[22] Filed: Sep. 23, 1996

Related U.S. Application Data

[63] Continuation of Ser. No. 404,016, Mar. 14, 1995, abandoned.

[51] Int. Cl.⁶ .................................................. C02F 1/72
[52] U.S. Cl. .................... 210/758; 210/749; 210/908; 562/17
[58] Field of Search .................... 210/758, 908, 210/749; 562/17

[56] References Cited

U.S. PATENT DOCUMENTS

| | | | |
|---|---|---|---|
| 3,969,398 | 7/1976 | Herschman | 260/502.5 |
| 4,104,162 | 8/1978 | Junkermann et al. | |
| 4,216,088 | 8/1980 | Juferov et al. | |
| 4,330,487 | 5/1982 | Redmore et al. | 210/700 |
| 4,338,196 | 7/1982 | Mayerle | 210/610 |
| 4,340,490 | 7/1982 | Junkermann et al. | 210/759 |
| 4,370,241 | 1/1983 | Junkermann et al. | 210/759 |
| 4,724,103 | 2/1988 | Gentilcore | 260/502.5 |
| 5,108,621 | 4/1992 | Robins | 210/728 |
| 5,244,581 | 9/1993 | Murphy | 210/756 |

FOREIGN PATENT DOCUMENTS

| | | | |
|---|---|---|---|
| 0130857 | 11/1978 | Japan | 210/749 |
| A-58043283 | 3/1983 | Japan | |
| 0842045 | 6/1981 | U.S.S.R. | 210/749 |

OTHER PUBLICATIONS

T. Mizuno et al—Nippon Nogei Kagaku Kaishi 44(7): 324-331 (1970).

Primary Examiner—Neil McCarthy
Attorney, Agent, or Firm—Monsanto Company; Arnold, White & Durkee

[57] ABSTRACT

A process is provided for selectively converting formaldehyde in an acidic organic waste aqueous stream in the most part to formose sugars rather than to alkali metal formate and methanol by reacting the stream with a strong alkali base to provide a pH of at least about 8.5 and heating the resulting basic solution to a temperature of at least about 80° C. The formaldehyde is present in the waste stream in amounts between about 1000 ppm to 10,000 ppm.

20 Claims, 1 Drawing Sheet

TREATMENT OF A FORMALDEHYDE-CONTAINING WASTE STREAM

This application is a continuation of application Ser. No. 08/404,016 filed Mar. 14, 1995, now abandoned.

BACKGROUND OF THE INVENTION

The present invention relates to a process for treating an aqueous waste stream containing formaldehyde. More particularly, the present invention relates to a process for treating an aqueous waste stream containing formaldehyde and obtained from the production of N-phosphonomethyliminodiacetic acid, whereby the formaldehyde is converted into nontoxic compounds.

N-phosphonomethylglycine, known in the agricultural chemical industry as glyphosate, is a highly effective and commercially important herbicide, useful in controlling the growth of germinating seeds, emerging seedlings, maturing and established woody and herbaceous vegetation, and aquatic plants. N-phosphonomethylglycine and its salts are conveniently applied in an aqueous formulation as a postemergent herbicide for the control of numerous plant species. N-phosphonomethylglycine and its salts are characterized by broad spectrum activity, i.e., the control of a wide variety of plants.

Numerous methods are known in the art for the preparation of N-phosphonomethylglycine. For example, U.S. Pat. No. 3,969,398 to Hershman discloses a process for the production of N-phosphonomethylglycine by the oxidation of N-phosphonomethyliminodiacetic acid utilizing a molecular oxygen-containing gas as the oxidant in the presence of a catalyst comprising activated carbon.

In U.S. Pat. No. 4,724,103 to Gentilcore a process for preparing N-phosphonomethyliminodiacetic acid is disclosed. Such process involves sequentially reacting an alkali metal salt of iminodiacetic acid with a strong mineral acid to form the strong mineral acid salt of iminodiacetic acid and the alkali metal salt of the strong mineral acid and phosphonomethylating the iminodiacetic acid by reaction with formaldehyde and phosphorous acid to provide a mixture of N-phosphonomethyliminodiacetic acid and an alkali metal salt. The preferred alkali metal is sodium. After completion of the phosphonomethylation step, water is added to the reaction mixture in an amount sufficient to dissolve the alkali metal salt. Then, the resulting N-phosphonomethyliminodiacetic acid is separated as a precipitate by conventional techniques, such as filtration, centrifugation or the like. The liquid remaining after removal of the precipitate is a complex mixture of chemicals, including a significant amount of formaldehyde which is a substance of toxicological concern and is a suspected carcinogen. Converting the formaldehyde in the remaining liquid into environmentally acceptable nontoxic compounds in high yields is an obvious desideratum.

It is known that when formaldehyde is brought into reacting contact with an alkaline substance, two different and competing reactions may occur. One reaction is known as the Cannizzaro reaction, wherein two moles of formaldehyde proceed in an alkaline medium to produce one mole of formic acid and one mole of methanol. When the aqueous solution containing formaldehyde is treated with alkali metal bases the primary reaction products are methanol and the alkali metal salt of formic acid. The second reaction is known as the formose condensation, wherein formaldehyde proceeds in alkaline solution to produce a complex mixture of several kinds of monosaccharides (aldoses and ketoses) of different carbon numbers. As used herein, the term "formose sugars" is meant to describe known mixtures of low molecular weight polyhydroxyl compounds (polyhydric alcohols, hydroxy aldehydes and hydroxy ketones) which are normally formed in the condensation reaction of formaldehyde hydrate. The ratio at which the two above described reactions occur in the conversion of formaldehyde is a function of the base used and many other process parameters.

In converting formaldehyde in a waste process stream to an environmentally acceptable product, it has been found desirable to promote the formose condensation of formaldehyde to formose sugars and to suppress the Cannizzaro reaction of formaldehyde, since both the formic acid and methanol reaction products of the Cannizzaro reaction are significantly less environmentally friendly than the formose sugars resulting from the formose condensation reaction. Stated another way, from an environmental perspective, the disappearance of formaldehyde from the waste stream obtained in the production of N-phosphonomethyliminodiacetic acid from the reaction of disodium iminodiacetate, phosphorus trichloride and formaldehyde by the formose condensation reaction to yield formose sugars is much more preferred than having the Cannizzaro reaction to occur to yield methanol and formic acid.

The present invention provides a technically simple and direct process, wherein nearly all of the formaldehyde in the waste stream obtained from the reaction of disodium iminodiacetate, phosphorus trichloride and formaldehyde to produce N-phosphonomethyliminodiacetic acid is consumed by the formose condensation reaction and a minimal amount of the formaldehyde is consumed by the Cannizzaro reaction. This disproportionately high conversion of the formaldehyde into formose sugars is surprising and unexpected, since it was heretofore believed that the Cannizzaro reaction to convert formaldehyde to methanol and formic acid was the dominant reaction in the presence of alkali metal bases.

T. Mizuno et al reported in *Nippon Nogei Kagaku Kaishi* 44(7): 324–331 (1970) a study entitled "Sugar Formation By the Formaldehyde Condensation in the Presence of Inorganic and Organic Bases". The sugar forming abilities of $Ca(OH)_2$, $Ba(OH)_2$, $Sr(OH)_2$, $Mg(OH)_2$, $Pb(OH)_2$, KOH, NaOH and TlOH were compared with certain organic bases, such as pyridine. The tests of T. Mizuno et al were carried out at 60° C. in the 1.86M formaldehyde aqueous solution with the concentration of 0.2M of the various bases. It was confirmed that the alkaline earth metal hydroxides are better, and especially $Ca(OH)_2$ is the best catalyst, among the bases tested for the generation of the formose sugars. Using NaOH, a yield of formose sugars of only 11.3 percent was obtained.

SUMMARY OF THE INVENTION

In accordance with the practice of the present invention, an aqueous waste stream containing unreacted formaldehyde present in the amount of 1000 to 10,000 ppm and obtained from the manufacture of N-phosphonomethyliminodiacetic acid by the reaction of disodium iminodiacetate, phosphorus trichloride and formaldehyde is treated to convert a substantial amount of the formaldehyde (at least 75% conversion) to a complex mixture of formose sugars with limited conversion (20% or less) of the formaldehyde to a mixture of formic acid in the form of alkali metal formate and methanol. This autocondensation reaction is accomplished by adding to the said waste stream a sufficient amount of an aqueous solution of an alkali metal hydroxide, such as sodium hydroxide or potassium hydroxide, to provide the waste stream with a pH value of at least 8.5 and heating the resulting basic waste stream to a temperature of about 80° C. or higher but preferably not much higher than the reflux temperature of the resulting basic waste stream for a sufficient time, whereby the formaldehyde disappearance occurs almost entirely by the formose condensation route rather than by the Cannizzaro route. The waste stream is cooled and neutralized with a strong mineral acid to reduce the pH to an environmentally acceptable level.

BRIEF DESCRIPTION OF THE DRAWING

The attached drawing is a schematic representation of the practice of the present invention. Although the drawing illustrates a continuous process, it is obvious that the process of the present invention may be carried out either continuously or in batches.

DETAILED DESCRIPTION OF THE INVENTION

Figure 1:
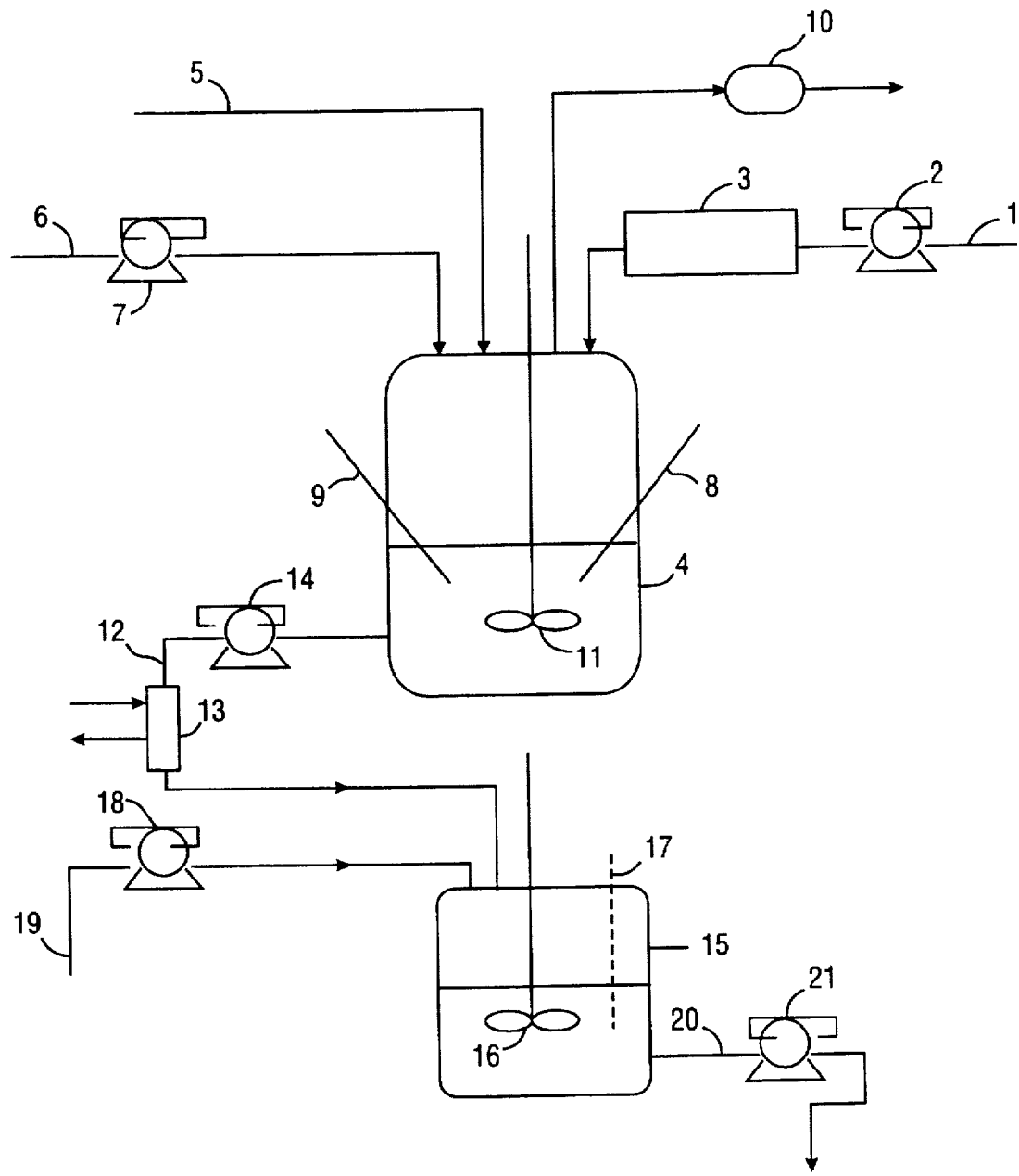

The waste stream containing undesirably high levels of formaldehyde which the practice of the present invention converts into environmentally acceptable products is obtained by the practice of the process of U.S. Pat. No. 4,724,103. In such process, disodium iminodiacetate (DSIDA) and phosphorus trichloride ($PCl_3$) are heated together in water to an elevated temperature to yield a slurry of the hydrochloride of iminodiacetic acid, sodium chloride and phosphorous acid. Thereafter, $CH_2O$ (as formalin) is slowly added. The resulting reaction mixture is cooled. Sodium hydroxide aqueous solution is added in an amount sufficient to minimize the solubility of N-phosphonomethyliminodiacetic acid which precipitates from solution. The mixture is filtered or centrifuged and the resulting solid material is recovered. The liquid from the isolation of N-phosphonomethyliminodiacetic acid is a waste stream containing formaldehyde, a compound of toxicological concern, selected organic phosphonic acids, sodium chloride and selected mineral acids of phosphorus. The practice of the present invention involves the conversion of the formaldehyde in the waste stream to a predominant mixture of formose sugars and converts the waste stream into a product which is more suitable for disposal.

With reference now to the attached drawing, numeral 1 in the flow chart denotes a line through which the waste stream is moved by means of pump 2 from a source not shown. The moving stream is heated as it flows through preheater 3 into reactor 4, the contents of which are optionally blanketed with an inert gas, such as nitrogen, supplied via line 5. Into the reactor 4 an aqueous solution of sodium hydroxide (~20%), moves through line 6 by means of pump 7.

Reactor 4 is equipped with a pH probe 8 and a temperature controller 9. The reactor may be equipped with an off gas collection system 10 and a stirrer 11. The pH of the contents of reactor 4 preferably is at least 8.5 and more preferably over 9.0 and most preferably in the range of about 9.5–12.5. The waste stream is further heated in the reactor, if needed, while being stirred to a temperature of at least 80° C., preferably at temperatures in the range of about 85° to 150° C., and most preferably between about 90° C. and the reflux temperature of 110° C. After at least 50% of the formaldehyde in the waste stream has been converted into formose sugars, the reaction mixture is transferred from reactor 4 via line 12 and moved through a heat exchanger 13 by means of pump 14. The reaction mixture is cooled in the heat exchanger and then conveyed into second reactor 15 which is equipped with a stirrer 16 and optionally a pH probe 17. In the second reactor, the reaction mixture is neutralized by adding a strong mineral acid, such as HCl or $H_2SO_4$ from a source not shown by means of pump 18 through line 19 into reactor 15. The neutralized product is removed from reactor 15 and is moved through line 20 by pump 21 to an acceptable disposal site. An analysis of the neutralized product reveals that as high as 95% of the formaldehyde values can be converted into environmentally acceptable formose sugars with no appreciable amounts of formic acid and methanol being formed from the formaldehyde in the waste stream. The pH of the neutralized product is reduced to an environmentally acceptable level.

An analysis of the initial waste stream treated in accordance with the present invention is typically as follows:

| Component | Weight Percent |
| --- | --- |
| Water | 68.0 |
| NaCl | 18.0 |
| Formic acid | 0.2 |
| Formaldehyde | 0.3 |
| $H_3PO_3$ | 1.6 |
| Organic Waste | 4.2 |

EXAMPLES 1–11

The process described above was carried out under a variety of reaction conditions with various waste streams having been obtained from the production of N-phosphonomethyliminodiacetic acid using the process of U.S. Pat. No. 4,724,103. The pH of the stream, the temperature of the stream, and the residence time of the stream in the reactor were varied. The concentrations of the formaldehyde in the streams as the result of the treatments and the presence of methanol before and after each treatment were noted. The data from the tests have been tabulated below. All tests were performed in a continuous mode for 5 hours. Data were collected every hour to ensure steady state conditions were maintained during the tests. Methanol analyses were obtained by use of a gas chromatography—headspace autosampler.

TABLE

| Example No. | Temperature (°C.)/pH | Residence Time (min) | Influent/ Effluent $CH_2O$ Conc. (ppm) | Influent/ Effluent MeOH Conc. (ppm) |
| --- | --- | --- | --- | --- |
| 1 | 84/10.7 | 5 | 2375/83 | 152/131 |
| 2 | 103/8.8 | 5 | 3869/496 | 183/176 |
| 3 | 103/9.75 | 5 | 2343/109 | 152/123 |
| 4 | 103/10.6 | 5 | 3863/97 | 183/164 |
| 5 | 85/10.7 | 12.5 | 2375/51 | 152/116 |
| 6 | 93/9.75 | 12.5 | 3869/114 | 183/136 |
| 7 | 84/10.7 | 20 | 3967/41 | 183/109 |
| 8 | 93/8.8 | 20 | 3823/300 | 183/180 |
| 9 | 103/8.8 | 20 | 2294/217 | 152/59 |
| 10 | 103/9.75 | 20 | 3882/83 | 183/76 |
| 11 | 102/10.7 | 20 | 2346/198 | 152/83 |

With regard to the operational parameters of the novel and useful process described herein in terms of the impact of pH, temperature, and residence time of formaldehyde removal from the waste stream, it has been found that using the above described continuous process a pH range of about 8.8 to about 10.7, a temperature range of about 84°–110° C. and a residence time in the reactor in the range of about 5–20 minutes provide excellent conversion of the formaldehyde in the aqueous waste stream to formose sugars. The selectivity of the conversion of the formaldehyde can be controlled such that less than one percent methanol and formate results.

The in-situ chemical conversion of the formaldehyde into the formose sugars as provided by the practice of the present invention has proved to be a most cost effective way to remove formaldehyde from aqueous waste streams. The formose reaction of the process of the present invention provides a convenient and effective conversion of formaldehyde to formaldehyde oligomer-based sugars. Due to the autocatalytic nature of the reaction, a continuous-mode process requiring a relatively short resident time of 5–10 minutes has been demonstrated to be technically feasible for the destruction of greater than 94% of the formaldehyde to form environmentally benign formose sugars. The environmental compatibility of the product resulting from the practice of the present invention has been demonstrated. Furthermore, the product does not have increased levels of methanol and alkali metal salt of formic acid which are the typical but undesirable products of the Cannizzaro reaction.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and description as set forth hereinabove but rather that the claims be construed as encompassing all the features of patentable novelty which reside in the present invention, including all features which would be treated as equivalents thereof by those skilled in the art to which the invention pertains.

What is claimed:

1. A process for selectively converting formaldehyde in an acidic aqueous stream associated with the manufacture of N-phosphonomethyliminodiacetic acid to formose sugars comprising the steps of:
   (a) adding an aqueous solution of a strong alkali base to said stream to provide a pH of at least about 8.5; and
   (b) heating the resulting basic solution to a temperature of at least about 80° C., thereby promoting the formose condensation of the formaldehyde to formose sugars while effectively suppressing the Cannizzaro reaction of the formaldehyde into formic acid and methanol.

2. The process of claim 1 wherein the pH of the aqueous stream is raised to a level at least 9.0.

3. The process of claim 2 wherein the basic solution is heated at a temperature above 90° C., wherein at least 50 percent of the formaldehyde in the stream is converted to formose sugars.

4. The process of claim 3 wherein the base is an alkali metal hydroxide.

5. The process of claim 4 wherein at least 94 percent of the formaldehyde in the stream is converted to formose sugars.

6. A process of treating an acidic aqueous stream containing organic waste comprising formaldehyde, and other wastes associated with the manufacture of N-phosphonomethyliminodiacetic acid comprising the steps of
   (a) adding an aqueous solution of an alkali metal hydroxide to said stream to provide a pH therein of at least about 8.5;
   (b) heating the resulting basic solution to a temperature of at least about 80° C., wherein at least 75 percent of the formaldehyde is converted to formose sugars;
   (c) cooling the resulting basic mixture; and
   (d) adding a strong mineral acid to the cooled mixture to lower the pH of the mixture to an environmentally acceptable level, thereby promoting the formose condensation of the formaldehyde to formose sugars while effectively suppressing the Cannizzaro reaction of the formaldehyde.

7. The process of claim 6 wherein the resulting pH of the aqueous stream of step (a) is over 9.0.

8. The process of claim 7 wherein the basic solution is heated to a temperature above 90° C.

9. The process of claim 8 wherein the alkali metal hydroxide is sodium hydroxide.

10. The process of claim 9 wherein at least 90 percent of the formaldehyde is converted to formose sugars.

11. The process of claim 10 wherein the strong mineral acid is hydrochloric acid or sulfuric acid.

12. A process for treating and disposing of an acidic aqueous stream containing organic and inorganic waste and obtained from the process of preparing N-phosphonomethyliminodiacetic acid by reacting sequentially an alkali metal salt of iminodiacetic acid with a strong mineral acid to form the strong mineral acid salt of iminodiacetic acid and the alkali metal salt of the strong mineral acid, phosphonomethylating the salt of iminodiacetic acid by reacting the same with formaldehyde and phosphorous acid to provide N-phosphonomethyliminodiacetic acid as a precipitate in the resulting aqueous waste stream, and separating the precipitated N-phosphonomethyliminodiacetic acid therefrom, the said aqueous waste stream containing organic and inorganic waste including formaldehyde comprising the steps of
   (a) adding an aqueous solution of an alkali metal hydroxide to said aqueous stream to provide a pH therein of at least about 8.5;
   (b) heating the resulting basic solution to a temperature of at least about 80° C., wherein a substantial amount of the formaldehyde is converted to formose sugars;
   (c) cooling the resulting basic mixture;
   (d) adding a strong mineral acid to the cooled mixture to lower the pH of the mixture to below 8.0; and
   (e) disposing the product of step (d) in an environmentally acceptable manner.

13. The process of claim 12 wherein the pH of the aqueous stream is over 9.0.

14. The process of claim 13 wherein the basic solution is heated to a temperature above 90° C.

15. The process of claim 14 wherein the alkali metal hydroxide is sodium hydroxide.

16. The process of claim 15 wherein at least 50 percent of the formaldehyde is converted to formose sugars.

17. The process of claim 16 wherein the strong mineral acid is hydrochloric acid or sulfuric acid.

18. The process of claim 17 wherein the basic solution is heated in the range of 84° to 110° C.

19. The process of claim 18 wherein the content of formaldehyde is in the range of 1000–10,000 ppm.

20. The process of claim 12 wherein the neutralized mixture of step (d) is without further treatment in an environmentally acceptable manner.

* * * * *